United States Patent [19]

Aoki

[11] Patent Number: 4,866,272

[45] Date of Patent: Sep. 12, 1989

[54] SURFACE ANALYZER FOR DETERMINING THE ENERGY DISTRIBUTION OF SCATTERED PROTON BEAMS

[75] Inventor: Masahiko Aoki, Kyoto, Japan

[73] Assignee: Nissin Electric Co., Ltd., Kyoto, Japan

[21] Appl. No.: 190,070

[22] Filed: May 4, 1988

[30] Foreign Application Priority Data

May 7, 1987 [JP] Japan ................................. 62-111162

[51] Int. Cl.$^4$ ...................... H01J 37/252; H01J 49/46
[52] U.S. Cl. ..................................... 250/309; 250/305
[58] Field of Search ................................ 250/309, 305

[56] References Cited

U.S. PATENT DOCUMENTS 4,584,474   4/1986   Franchy et al. .................... 250/305

OTHER PUBLICATIONS

Niftrik et al., Nuclear Instruments and Methods, vol. 93, No. 2 (1971), pp. 301–309.

Primary Examiner—Jack I. Berman
Attorney, Agent, or Firm—Finnegan, Henderson, Farabow, Garrett, & Dunner

[57] ABSTRACT

A surface analyzer for analyzing the atomic composition of the surface of sample. An ion source generates a proton beam. A magnet directs the proton beam through an accelerating device toward the sample for collision therewith. Protons that are scattered at an angle of 180° pass through the accelerating device in the reverse direction and are decelerated. The magnet directs the protons as a parallel beam to a position detecting device that indicates the position at which the proton beam strikes and energy loss of the protons can be determined.

6 Claims, 9 Drawing Sheets

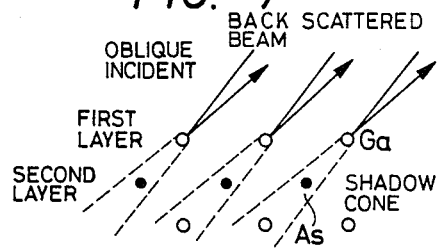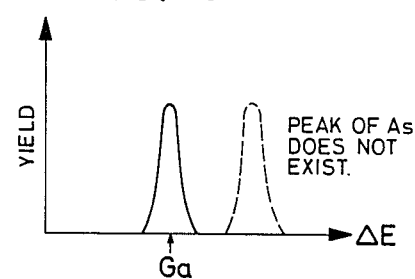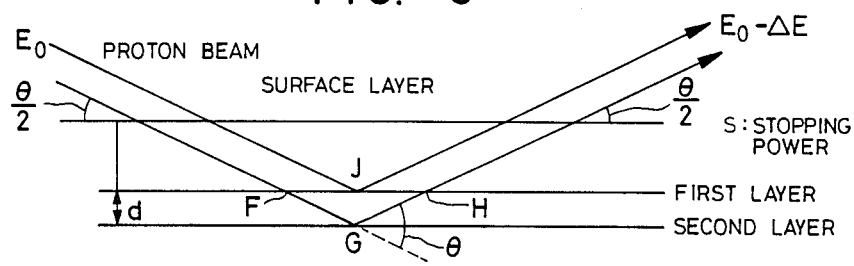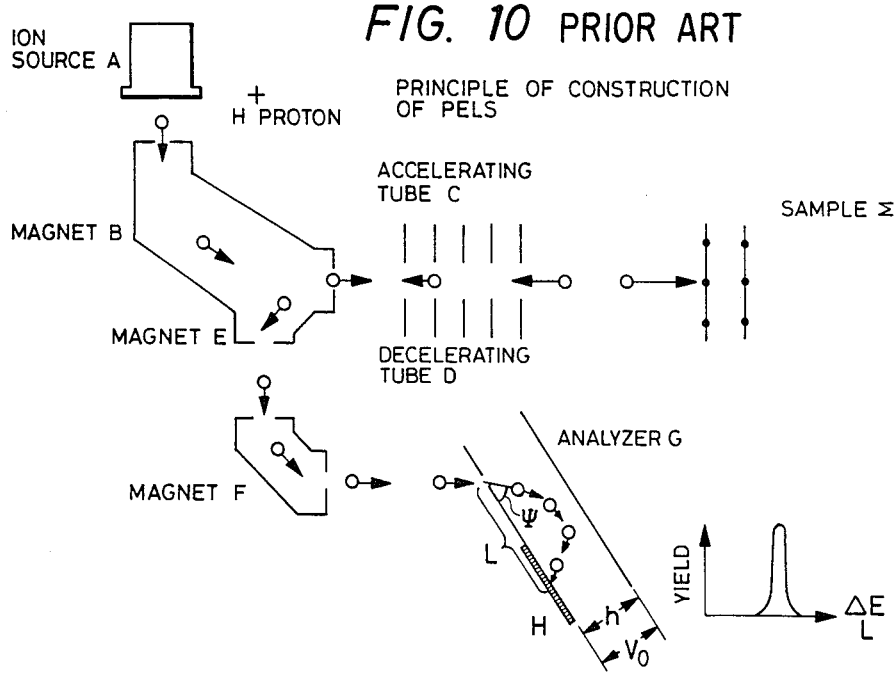

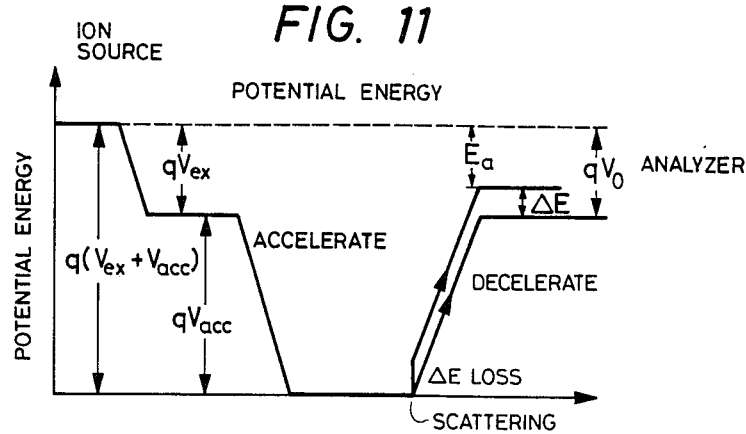
FIG. 11
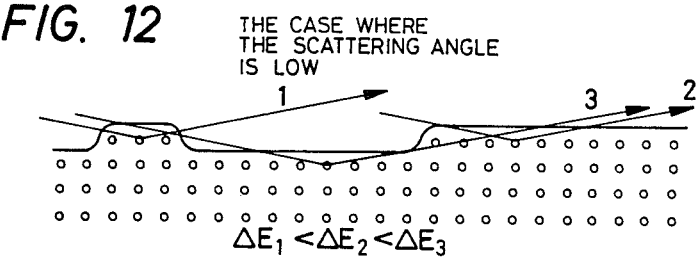
FIG. 12 THE CASE WHERE THE SCATTERING ANGLE IS LOW
$\Delta E_1 < \Delta E_2 < \Delta E_3$
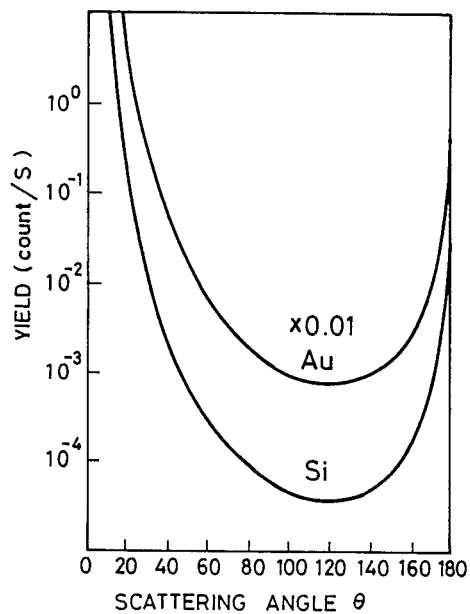
FIG. 13

SURFACE ANALYZER FOR DETERMINING THE ENERGY DISTRIBUTION OF SCATTERED PROTON BEAMS

FIELD OF THE INVENTION

The present invention relates to an improvement of an energy detector used in a surface analyzer to determine the enery distribution of scattered proton beams.

BACKGROUND OF THE INVENTION

A surface analyzer is an apparatus in which a sample to be analyzed is irradiated with accelerated proton beams. A scattering pattern of the proton beams caused by collisions with atoms in the sample which decelerate the protons is generated and the energy distribution of the decelerated proton beams is measured to identify the species of atoms on the surface of the sample, as well as to determine their proportions.

The crystalline structure of the bulk of a sample can be analyzed by X-ray diffraction. Techniques such as electron diffraction are also available for examining the cyrstalline structure of a near-surface area of the sample. None of these methods, however, are capable of providing the distribution of elements on the very surface of the sample, for example on the topmost or within the top two atomic layers.

The present inventors developed a technique called PELS (proton energy loss spectroscopy) as a method for measuring the elements on the topmost or within the top two atomic layers of a sample. PELS is a new technique of measurement and its operating principles will be briefly described.

Suppose, as shown in FIG. 3, a proton of mass number m, moving with velocity U hits an atom of mass M at rest. After collision, the proton is scattered by the atom and glances off at velocity V along a path deflected from its original path by an angle $\theta$ while the atom moves at velocity W in another direction defined by angle $\Phi$. Since momentum is conserved in both the x- and y-directions, the following two equations are established:

$$mU = mV \cos\theta + MW \cos\Phi \quad (1)$$

$$0 = mV \sin\theta + MW \sin\Phi \quad (2)$$

If the collision is completely elastic, kinetic energy is conserved so that;

$$(1/2)mU^2 = (1/2)mV^2 + (1/2)MW^2$$

Eliminating W from Eqs. (1) to (3), $$(\Gamma+1)V^2 - 2U\cos\theta V - (\Gamma-1)U^2 = 0 \quad (4)$$

Then, $$V = \frac{\cos\theta \pm \sqrt{\Gamma^2 - \sin^2\theta}}{\Gamma + 1} U \quad (5)$$

where $$\Gamma = (M/m) \quad (6)$$

The minus sign in Eq. (5) indicates scattering at angle $(\pi - \theta)$. Only the plus sign should be taken to consider scattering at angle $\theta$.

The proton will lose part of its energy as a result of scattering. For the same scattering angle a collision with a lighter atom will cause greater energy loss than a collision with a heavier atom. Therefore, by measuring the energy loss occurring in the proton, the identity of the atom against which it collided can be determined.

If the kinetic energy of the proton before a collision is written as $E_0$, $$E_0 = (1/2)mU^2 \quad (7)$$

and if the energy of the proton after collision is written as $E_1$, $E_1$ is always smaller than $E_0$. The ratio of $E_1/E_0$ is called the coefficient of attenuation K. The following equations will be established:

$$E_1 = KE_0 \quad (8)$$

$$K = \frac{(\cos\theta \pm \sqrt{\Gamma^2 - \sin^2\theta})^2}{(\Gamma + 1)^2} \quad (9)$$

It is not $\theta$ but $\Gamma$ which is a variable because $\theta$ is uniquely determined by the experimental apparatus employed.

The present inventors first developed a PELS apparatus of low scattering angle ($\theta \cong 0$) as disclosed in Unexamined published Japanese application No. 180945/1984 (published Oct. 15, 1984) and 151958/1986 (published July 10, 1986).

The low scattering-angle apparatus has the disadvantage that it is highly susceptible to the surface state of a sample to be analyzed as will be apparent from FIG. 12. In addition to single scattering, double scattering might also occur on account of asperities on the surface of the sample. Another disadvantage of the use of a low scattering-angle is its low resolution since K is not highly sensitive to $\Gamma$ as suggested by Eq. (9).

The operating theory of PELS is basically set forth in Eq. (9) but this assumes attenuation by single scattering and is not valid if multiple scattering occurs.

Low scattering angles were selected for the simple reason that they produce high proton yield. FIG. 13 shows the proton yield vs. scatterring angle $\theta$ for Au and Si. The proton yield as relative against the scattering angle is determined by geometric factors and will not depend upon the physical properties of a specific atom. As shown in FIG. 13, a maximum yield is also attained at $\theta = 180°$. Eq. (9) shows that at $\theta = 180°$, the highest resolution can be attained with respect to $\Gamma$. In this case where $\theta = \pi$, the coefficient of attenuation K can be rewritten as:

$$K = \left(\frac{\Gamma - 1}{\Gamma + 1}\right)^2 \quad (10)$$

The parameter $\Gamma$ denotes the ratio of the mass, M, of the atom to the mass, m, of the proton. If the slight difference between the mass of the proton and the atomic mass unit is disregarded, $\Gamma$ may safely be referred to as the mass number of the atom of interest.

For various elements, the $\Gamma$ values and hence K values can be determined. The mass numbers, as defined above, of atoms are listed below together with corresponding K values:

Al: $\Gamma = 26.98$, K=0.8621
Ga: $\Gamma = 69.72$, K=0.94422

As: $\Gamma = 74.9$, $K = 0.94799$.

In this way, the K values of all elements of atoms can be easily calculated.

The foregoing discussion can be summarized as follows. If the kinetic energy, $E_1$, of a proton after collision is measured, K can be determined by calculating the ratio of $E_1$ to $E_0$. This leads to the determination of $\Gamma$ value and hence to the identification of the atom against which the proton collided. Then, the abundance of that particular atom in a sample of interest can be determined from the energy spectrum. In most cases, $E_0$ is selected at about 100 keV.

The principles of PELS are very simple as described above. In order to enable measurements by PELS, the proton must be scattered only once. Instead of direct measurement of $E_1$, the energy loss $\Delta E[=(1-K)E_0]$ may be measured. The name "PELS" derives from this measurement of the energy loss distribution of a proton.

As shown in FIG. 4, when protons having mass m are scattered by a heavy atom M, an area where no protons exist will occur in the forward direction and this is generally referred to as a shadow cone. Few of the protons travelling a far distance from the atom M are scattered and those travelling near the atom M are highly likely to be scattered. This is the mechanism behind the formation of a shadow cone.

If an x-axis is assumed to lie in the direction in which a proton travels and a y-axis is assumed to lie in a direction perpendicular to that direction of travel, a repelling Coulomb force acting between the atom and the proton, will produce a shadow cone with a shape that can be expressed by:

$$Y = 2\left(\frac{Zze^2 x}{E_0}\right)^{\frac{1}{2}} \quad (11)$$

where e is the elementary quantity of a load, z is a charge on the proton, and Z is a charge on the atom (with e being a unit).

By using the shadow cone, one can identify the atoms in the top monolayer of a sample, as is clear from the following discussion. Suppose proton beams are directed perpendicularly to the surface of a GaAs sample as shown in FIG. 5. The protons are scattered both by Ga and by As, so two peaks occur in the distribution of proton energy as shown in FIG. 6.

If proton beams are impinged on the sample at an angle as shown in FIG. 7 such that the atoms of the element in the next to the top layer are located within the shadow cones created by the atoms of the element in the topmost layer, the distribution of proton energy loss will have only the peak corresponding to the atoms in the topmost layer. With reference to FIG. 8, only the Ga peak appears. This result shows that Ga atoms are present in the topmost layer of the sample.

When proton beams are launched into a sample, proton energy loss occurs as a result of collisions not only with atoms but also with electrons. The energy loss due to collisions with electrons is proportional to the distance the proton travels in the sample. This will be explained more specifically with reference to FIG. 9.

If proton beams are launched into a sample at an angle $\theta/2$ with respect to surface layers, the proton energy loss differs between two cases. One case is when an incident proton is scattered at point J in the topmost layer and is reflected at angle $\theta/2$, and the other case is where the incident proton is scattered at point G in the next to the top (second) layer. The differential energy loss is expressed as:

$$\Delta E = 2dS \cos ec(\theta/2) \quad (12)$$

where d is the distance between two layers and S is the stopping power of electrons. The value of $\Delta E$ increases with decreasing $\theta$. Even if $\theta = \pi$, $\Delta E$ is 112 eV assuming that d = 5.6 Å and S = 10 eV/Å.

The above discussion shows that even in the case of normal ($\theta = \pi$) launching of proton beams, the energy lost by the protons scattered from the topmost layer differs by about 100 eV from the loss due to scattering in the second layer. In other words, even if the atom of mass M which is the principal factor of proton scattering is the same, protons will lose energy by different degrees in the topmost and second layers.

By decreasing $\theta$, $\Delta E$ can be sufficiently increased to provide for distinction between proton scattering by dissimilar atoms in the topmost and second monolayers.

FIG. 10 shows the general layout of a prior art PELS measuring system in the case where the scattering angle $\theta$ is 180°. Protonic beams extracted from an ion source A are subjected to mass separation in a magnet B. Only monovalent proton ions are selected and introduced into an acceleration tube C for acceleration.

The proton beams acquiring a kinetic energy of $E_0$, which is the sum of the extraction energy Eex and the acceleration energy Eacc provided by the acceleration tube C, will impinge on a sample $\Sigma$. The protons are scattered by atoms in the surface of the sample $\Sigma$.

Only the protons scattered at angle $\theta = \pi$ will travel backward through the accelerating tube. Those which were scattered at angle $\theta \neq \pi$ will collide against the wall of the chamber, make transition from the ionic to the neutral molecule ($H_2$) form, and be discharged from the chamber. The protons scattered at angle $\theta = \pi$ and that travel backward through the accelerating tube are decelerated. In other words, the accelerating tube now works as a decelerating tube.

The decelerating energy Edec is equal to the accelerating energy Eacc:

$$Eacc = Edec \quad (13)$$

One of the advantages of the case where $\theta = \pi$ is that a common tube can be used both as an accelerating tube C for accelerating proton beams and as a decelerating tube D for decelerating proton beams.

The decelerated proton beams are bent by 90° with a magnet F. The protons are thereafter launched into an analyzer G at an angle. Two magnets E and F are necessary in order to converge the proton beams whose energy has a variance due to scattering loss $\Delta E$.

The convergent proton beams are subjected to energy detection in the analyzer G. A voltage $V_o$ is applied between two parallel electrode plates. A proton launched into the analyzer through a slit will travel on a parabolic path and fall into either one of the channels in a microchannel plate H. The channel into which the proton has fallen will indicate the distance L from the slit to the falling position of the proton, and hence the kinetic energy of the proton at the time that it was launched into the analyzer.

The distance L in the analyzer G increases as the kinetic energy of the proton increases. If the kinetic energy of the proton projecting onto the slit in the analyzer G is written as Ea, the angle formed between the incident proton beam and the electrode plate with the slit as $\Psi$, the distance between the two parallel electrode plates as h, and the electrostatic voltage applied between the plates as $V_o$, then L is expressed as:

$$L = \frac{2Eah\sin(2\psi)}{mzeV_o} \quad (14)$$

The distribution of distance L indicates the distribution of proton energy Ea, thereby enabling the measurement of proton energy distribution.

All the components of the system shown in FIG. 10 are placed in high vacuum. The sample $\Sigma$ must be in an ultrahigh vacuum. If this requirement for vacuum is not met, protons impinging on the molecules of a gas will lose energy and the scattering loss $\Delta E$ due to the sample $\Sigma$ cannot be correctly determined.

For the sake of simplicity, the vacuum chamber and the evacuation unit are omitted from FIG. 10.

The change in the energy of a proton is described hereinafter with reference to FIG. 11 which shows the potential energy of the proton as a function of its position during movement (assumed to be left to right in FIG. 11).

A proton ion is extracted from the ion source at an extracting volage of Vex. The proton has a charge q, which produces a potential energy of qVex. When the proton leaves the ion source, this energy changes to kinetic energy.

The proton is accelerated in the acceleration tube C at an accelerating voltage of Vacc. The proton emerging from the acceleration tube toward the sample $\Sigma$ has a kinetic energyof q(Vex+Vacc), which is equivalent to $E_o$ and is approximately 100 keV.

The proton beam impinges on the sample and is scattered therefrom, losing an energy of $\Delta E$. The scattered proton beam travels backward through the accelerating tube and loses kinetic energy equal to qVacc.

The proton beam, when it enters the analyzer G, has a kinetic energy Ea expressed as follows:

$$Ea = qV_o - \Delta E \quad (15)$$

where $V_o$ is equal to the extracting voltage Vex or may be described as the energy of proton launching into the analyzer G when the energy loss is assumed to be zero.

The value of Ea is set to be about 0.5 keV and the energy of the scattered proton Es, which is written as:

$$Es = q(Vex + Vacc) - \Delta E \quad (16)$$

is set to be about 100 keV.

Theoretically, Ea should be a variable. In practice, the atom to be analyzed is preliminarily determined and Vacc is determined in such a way that Ea associated with this atom will be about 0.5 keV.

FIG. 14 is a schematic view showing the general layout of PELS equipment. Proton beams issuing from an ion source are focused by an einzel lens, deflected by a magnet and accelerated by an accelerating/decelerating tube. A sample to be analyzed is set in an ultrahigh vacuum chamber and can be handled with a manipulator. The accelerated proton beams are converged with a Q lens and subsequently impinge on the sample in the ultrahigh vacuum chamber. Among the protons scattered from the sample surface, those scattered at $\theta = 180°$ emerge from the ultrahigh vacuum chamber and are decelerated. The decelerated proton beams are bent by 180° by magnets 1 and 2 and enter an analyzer for measurement of energy loss $\Delta E$.

The foregoing is intended to explain the principles of PELS, the composition of PELS equipment, and the mechanism of its action. The present invention relates to an improvement of a section of PELS equipment for measuring the energy loss, $\Delta E$, of a proton beam.

In the prior art system, a dc voltage $V_o$ is applied between two parallel electrode plates in such a way that a proton will fly on a parabolic path and the distance it travels is used as a basis for measurement of proton energy Ea in the analyzer G which depends on voltage for energy measurement.

The analyzer shown schematically in FIG. 10 employs two magnets. A prior art analyzing system using two magnets is shown schematically in FIG. 15. A proton beam scattered from the sample and decelerated by a decelerating tube D is bent by 90° in magnet E and bent by another 90° in magnet F. This can be realized by arranging the two magnets in such a way that the angle of intersection between the beam and the oblique side of each magnet is 45°.

Even if two protons have different energies, they have the same cyclotron angular frequency in a magnetic field. In addition, the kinetic energy of protons is invariable in a magnetic field. Therefore, if a proton is supposed to move on a circular orbit, the radius of the circle is proportional to its velocity, and the time required to travel a given portion (arc) of the circle is the same if the central angle is the same.

The advantage of using two magnets having an oblique angle of 45° is that protons having different energies can be converged into a single fine beam. This beam is launched into an electrostatic analyzer G through a fine slit at an angle of 45°.

The distance L in the analyzer is determined by Eq. (14).

The energy measuring system of the type described above is adopted in the PELS equipment shown in co-assigned Japanese Patent Application No. 164299/1986 (filed July 12, 1986). An analyzing system using one magnet (also prior art) is shown schematically in FIG. 16. This system uses one magnet with an oblique angle of 45°. When scattered protons are launched into this magnet at 45°, those having the smaller energy will travel on a circular path with a small radius of curvature, and those having the greater energy will travel on a circular path with a large radius of curvature.

In this way, proton beams can be separated spatially. The separated beams are launched into a wide electrostatic analyzer G through an elongated slit. As in the case of a two magnet analyzer, the distance L travelled by protonss in the analyzer is determined by Eq. (14).

The obvious advantage of the system shown in FIG. 16 is that the number of magnets needed is one, rather than two. An energy measuring system of the single magnet type described is shown in co-assigned Japanese Patent Application No. 299269/1986 (filed Dec. 16, 1986).

The prior art system for measuring the proton energy depends on an electrostatic voltage for changing the direction of the travel of protons and this has caused several problems. For example, in the electrostatic analyzer, the direction in which voltage is applied is not perpendicular to the direction of motion of the proton beams. A faster proton beam having a long flight will fly to a point close to the positive electrode plate. Since this should not happen, the distance between the two electrodes must be increased but then the size of the electrostatic analyzer is increased. Not only does this increase the cost of the analyzer but also the load on the evacuation unit is increased and additional vacuum pumps must be installed.

Moreover, both the parameters of the magnetic field H of a magnet and the voltage $V_o$ of the electrostatic analyzer G must be adjusted on the prior art systems. The need to adjust these parameters introduces complexity. For instance, if the magnetic field of magnet E is increased in the measuring system shown in FIG. 15, the beam emerging from this magnet has been bent 90° but at the same time, it has been displaced more outwardly than when the magnet is small. Unless the magnetic field of magnet F is increased correspondingly, the beam emerging from magnet F will be offset too much to pass through the slit 5.

In the case of the one-magnet system shown in FIG. 16, a wide electrostatic analyzer is necessary. Furthermore, the width of the microchannel plate must also be increased. This leads to a very expensive and hence uneconomical analyzer.

SUMMARY OF THE INVENTION

An object of the present invention is a surface analyzer capable of accurately analyzing the atomic composition of the surface of a sample.

Another object of the present invention is a surface analyzer that requires a single magnet to direct a proton beam from an ion source to a sample and to direct protons scattered at an angle of 180° following collision with the sample as parallel proton beams to a position detector.

A further object of the present invention is a surface analyzer that does not require an electrostatic energy analyzer.

These and other objects are accomplished by a surface analyzer for analyzing the atomic composition of the surface of a sample, comprising an ion source for generating protons, accelerating/decelerating means for accelerating protons moving therethrough toward the sample and decelerating protons moving therethrough away from the sample after collision with the sample and scattering at an angle of 180° with respect to the sample, a magnet for directing protons from the ion source to the accelerating/decelerating means for accelerating toward the sample and for forming parallel beams of the protons passing through the accelerating-/decelerating means following scattering at an angle of 180° following collision with the sample, and proton detecting means for receiving the parallel proton beams and for indicating the position at which the parallel proton beams are received such that the kinetic and energy loss of protons that collide with the sample and are scattered at an angle of 180° may be determined.

BRIEF DESCRIPTION OF THE DRAWINGS

The manner by which the above objects, and other objects, features, and advantages of the present invention are attained will be fully apparent from the following detailed description when considered in view of the drawings, wherein:

FIG. 7 is a sketch of the top few layers of a GaAs crystal showing proton beams that are incident and scattered obliquely in PELS;

FIG. 8 is a diagram of proton energy loss that occurs in PELS when proton beams are incident in the direction indicated in FIG. 7;

FIG. 9 is a scattering cross-sectional diagram showing how the topmost layer of a sample can be distinguished from the next to the top layer in terms of the increase in proton energy loss due to collisions with electrons;

FIG. 10 is a sketch showing the operating principles of PELS;

FIG. 11 is a diagram showing the potential energy profile of protons;

FIG. 12 is a sketch showing a proton beam scattered at a small angle;

FIG. 13 is a graph showing the proton yield vs. scattering angle for Au and Si;

DETAILED DESCRIPTION OF THE INVENTION

Figure 1:
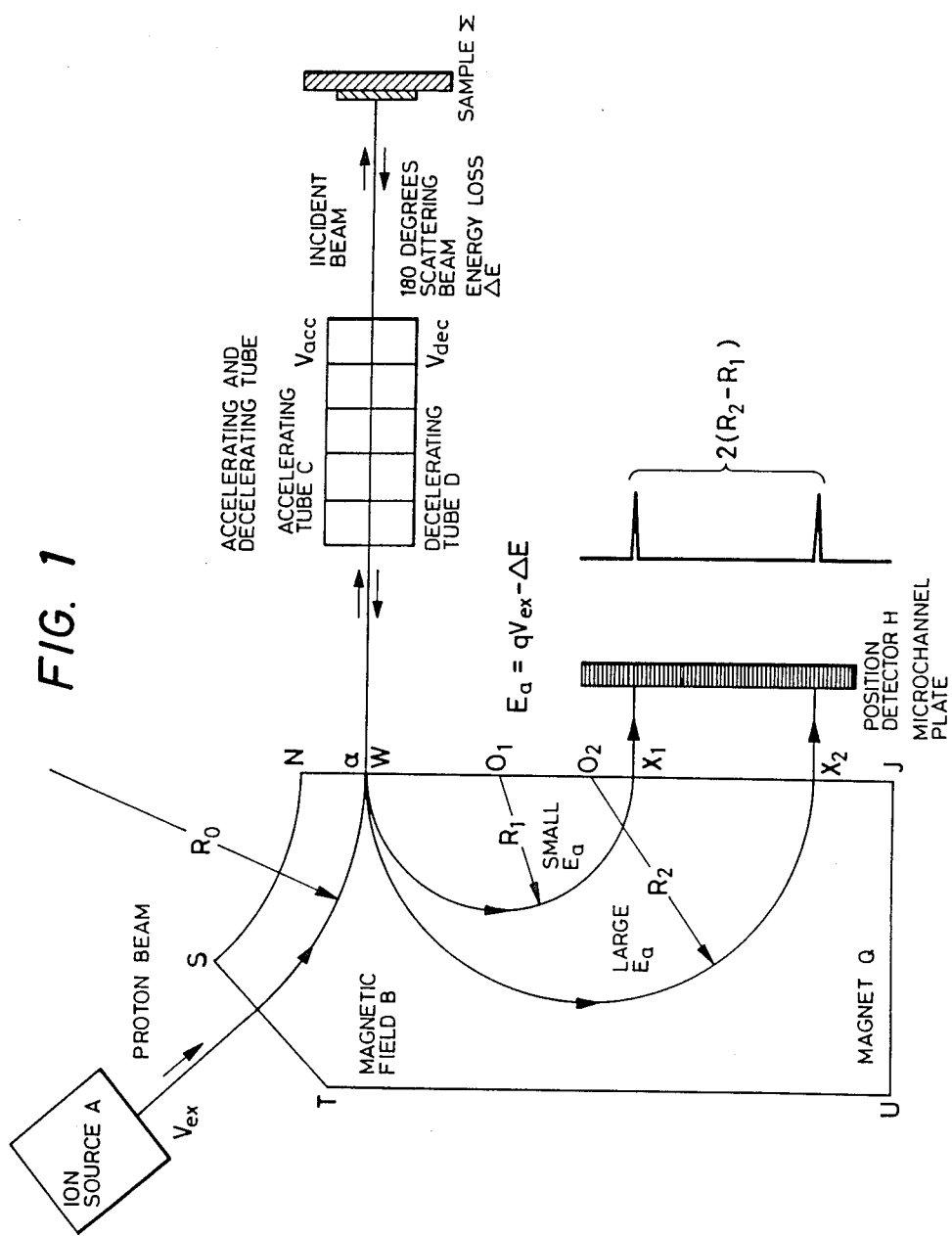
FIG. 1 shows the general layout of the surfaces analyzer of the present invention.

In order to know the proton energy Ea, proton beams must be separated spatially. In the prior art, an electrostatic analyzer that uses a voltage $V_o$ to relate energy Ea to distance L has been employed. The electrostatic analyzer suffers from the disadvantages already described sbove.

In the present invention, a magnetic field H, not a voltage, is used to achieve spatial separation of proton beams having different energies. The prior art also uses magnets to bend proton beams but not to achieve spatial separation of proton beams having different kinetic energies. In the present invention, a magnetic field is used for the specific purpose of spatially separating protons having different energies. A position detector composed of a microchannel plate is also used in the present invention.

The composition of the surface analyzer of the present invention is described hereinafter with reference to FIG. 1. The apparatus is entirely accommodated in a vacuum chamber and held in high vacuum. The evacuation unit is not shown in FIG. 1.

Instead of three magnets B, E and F used in the prior art system shown in FIG. 10, only one magnet Q is used in the system of the present invention. In the absence of an electrostatic analyzer, the position of a proton beam emerging from the end of the magnet Q is directly measured with a position detector H. The other aspects of the present invention are substantially the same as the prior art. In the ion source A, a gas such as hydrogen gas is ionized to produce protons, which are accelerated by an inter-electrode voltage Vex and emerge from the ion source A. The emerging protons are bent by the magnet Q with a curvature radius of Ro.

Bending the proton beams by magnet Q is necessary because the scattering angle $\theta$ is 180°. Since the direction in which the proton beams are incident on the sample is the same as the direction in which they are scattered from the sample the magnet is necessary to separate the incident beam from the scattered beam. If the scattering angle is not 180°, the incident beam need not be passed through the magnet. The present invention of course includes the case where $\theta \neq 180°$. The shape of magnet Q is a slightly deformed pentagon defined by points JNSTU.

The protons from the ion source A are launched into the magnet through side ST and travel on a curved path parallel to side SN. The protons emerging from side NJ will go straight through the accelerating tube C where they are accelerated and directed against the sample $\Sigma$. The incident protons collide with atoms in the surface of the sample 93 and are scattered, losing energy $\Delta E$. Those protons which were scattered at angle ($\theta$) of 180° will travel backward on the same path as that of the incident beam and are decelerated by the decelerating tube D. The decelerating energy is equal to the accelerating energy because the scattered protons travel through the same accelerating/decelerating tube.

The scattered proton beams have a kinetic energy of Ea which is expressed as:

$$Ea = qV_o - \Delta E \quad (17)$$

were $qV_o$ is constant but $\Delta E$ is not and varies with the atom against which the proton collides. Therefore, Ea is not constant and takes on as many values as the number of atoms with which the proton is to collide.

The scattered proton beams reenter the magnet at point W on side NJ. The central angle of the circular orbit on which the proton beam travels through the magnet is determined by the angle of intersection $\alpha$ between the straight line E$\Sigma$ and side NJ of the magnet. The portion WJ of side NJ must be a straight line. For the sake of the simplicity in design, NJ can also be made a straight line. However, it is not absolutely necessary that NJ intersects the beam line W$\Sigma$ at angle ($\alpha$) of 90°.

The cyclotron angular frequency $\Omega$ of a proton which is a free particle with charge q and mass m is given by the following equation in a magnetic field with a flux density of B:

$$\Omega = qB/mc \quad (18)$$

where c is the velocity of light in vacuum. The value of $\Omega$ is independent of the proton energy.

Two protons having different energies have the same cyclotron angular frequency in a magnetic field. Therefore, given the same time, the central angle of a circular orbit travelled by protons is the same.

It should, however, be noted that the cyclotron radius R varies with proton energy. If the velocity of a proton is written as v, $$v = R\Omega \quad (19)$$

$$(1/2)mv^2 = Ea \quad (20)$$

Therefore, the cyclotron radius R is:

$$R = \frac{1}{\Omega}\sqrt{\frac{2Ea}{m}} \quad (21)$$

$$= \frac{c}{qB}\sqrt{2mEa} \quad (22)$$

Eq. (22) is a statement using the gauss unit system, in which:
C = 3 × 10$^{10}$ cm/sec
m = 1.67 × 10$^{-24}$ g
q = 4.8 × 10$^{-10}$ cgsesu.

The unit of Ea in Eq. (22) is the erg which can be related to eV by the following equation:

$$1 \text{ erg} = 10^{12}/1.6 \text{ } eV \quad (23)$$

Therefore, Ea is expressed in terms of eV as follows:

$$R = 144 \frac{\sqrt{Ea}}{B} \text{ (cm)} \quad (24)$$

or $$R = \frac{1}{0.69} \frac{\sqrt{Ea}}{B} \text{ (m)} \quad (25)$$

where the unit of flux density B is gauss.

As evident from Eq. (25), a proton having a higher energy describes a circular path with a greater radius of curvature. The square root of proton energy is proportional to the radius of the circular path.

The proton as it emerges from the ion source has an energy of eVex. If the radius of the circular orbit on which this proton moves is written as Ro, the radius for the scattered proton which is dependent on $\Delta E$ is given by:

$$R = \sqrt{\frac{qVex - \Delta E}{qVex}} Ro \quad (26)$$

Therefore, the scatttered proton will travel on a circular path having a small radius if it has suffered a great energy loss, and it will travel on a circular path having a large radius if the energy loss is small.

In the case where $\alpha = 90°$, a scattered proton beam emerges from the magnet at point X on side NJ. In this case, the following equation is valid:

$$WX = 2R \quad (27)$$

Point X is close to point W if the beam has suffered a great energy loss, and the two points are distant from each other if the energy loss is small.

Since the scattered proton beam emerges from the magnet perpendicularly to side NJ, the position X on which the proton is launched into the microchannel plate (MCP) H is expressed as:

$$X = 2\left(1 - \frac{\Delta E}{q\text{Vex}}\right)^{\frac{1}{2}} Ro + (\text{const}) \quad (28)$$

$$X = \frac{288 (q\text{Vex} - \Delta E)^{\frac{1}{2}}}{B} + (\text{const}) \quad (29)$$

where Ro is not included.

Comparing Eq. (14) with Eq. (28) or (29), it can be seen that in the electrostatic analyzer, energy Ea is proportional to distance I, whereas in the present invention, the square root of Ea is proportional to flight 2R.

As shown in FIG. 1, proton beams pass through the magnet Q on three circular paths having different radii $R_0$, $R_1$ and $R_2$. These radii are respectively expressed by Eqs. (30), (31) and (33), which are obtained by substituting the energies of the respective proton beams as Ea into Eq. (25):

$$R_1 = \frac{\sqrt{q\text{Vex}}}{0.69B} \quad (30)$$

$$R_1 = \frac{\sqrt{q\text{Vex} - \Delta E_1}}{0.69B} \quad (31)$$

$$R_2 = \frac{\sqrt{q\text{Vex} - \Delta E_2}}{0.69B} \quad (32)$$

A microchannel plate (MCP) is used as a position detector in the present invention. This has an array of fine (micro) channels each being capable of multiplying one incident protonic ion by a factor of about $10^9$. This enables identification of the position where protons have fallen. Even a single protonic ion can be detected. The only requirement that should be met is that the energy of an incident proton be greater than a certain threshold value Et. If the energy of an incident proton is smaller than Et, a low amplification (multiplication) factor will result. This condition may be expressed as:

$$Ea > Et \quad (33)$$

If this condition is met, the number of protonic ions is proportional to the amount of electric current detected by the microchannel plate.

Suppose that a proton beam impinging on the sample has an energy of Eo=q(Vex+Vacc). The energy loss $\Delta E$ is expressed as:

$$\Delta E = (1-K)Eo \quad (34)$$

where $$\text{where } K = \left(\frac{\Gamma - 1}{\Gamma + 1}\right)^2 \quad (35)$$

where T is the mass number.

The value of qVex must be greater than (Et+$\Delta E$). Suppose the following values as Eo, Et and Ro:
 Eo=q(Vex+Vacc)=100 keV
 Et=3 keV
 Ro=250 mm With qVex being varied as 34.2 keV, 15.2 keV, 8.6 keV, 7.1 keV, 6.1 keV, 5.1 keV and 4.9 keV, the value of peak position X can be determined from Eq. (28) for various elements having the following values of $\Gamma$. The term (const) in Eq. (28) is assumed to be zero:

| | | |
|---|---|---|
| r = 11 | B | K = 0.6944 |
| r = 31 | P | K = 0.8789 |
| r = 70 | Ga | K = 0.9445 |
| r = 96 | Mo | K = 0.9592 |
| r = 128 | Te | K = 0.96923 |
| r = 184 | W | K = 0.97849 |
| r = 209 | Bi | K = 0.981043. |

Eq. (28) can be rewritten as follows:

$$X = 50\left(1 - \frac{(1-K) \times 100}{q\text{Vex}}\right)^{\frac{1}{2}} \quad (36)$$

Figure 2:
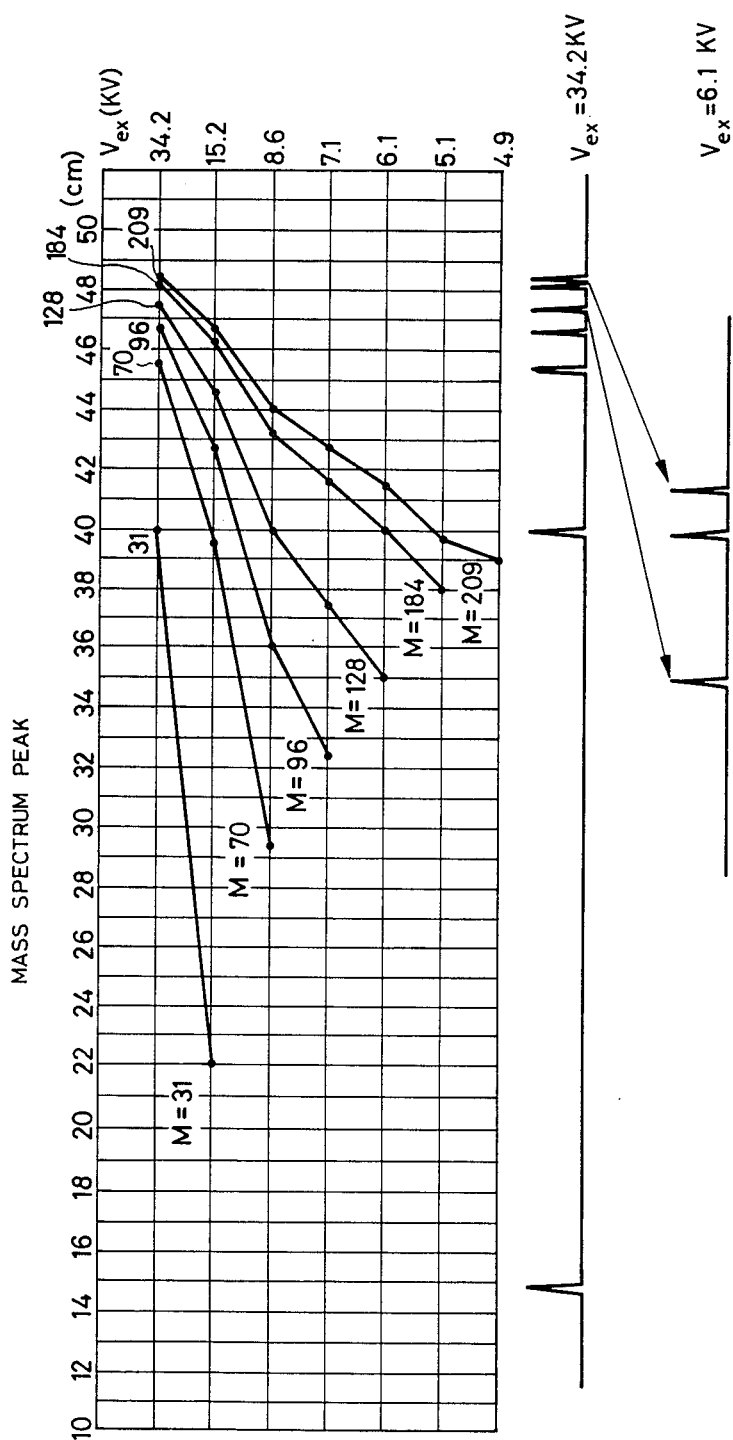
FIG. 2 is a graph showing spectrum peaks for atoms with atomic numbers of 31, 70, 96, 128, 184, and 209 when atomic mass spectrum measurements were conducted with the apparatus of the present invention, with ion extracting voltage Vex being used as a parameter and varied as 34.2 kV, 15.2 kV, 8.6 kV, 7.1 kV, 6.1 kV, 5.1 kV and 4.9 kV.
Figure 3:
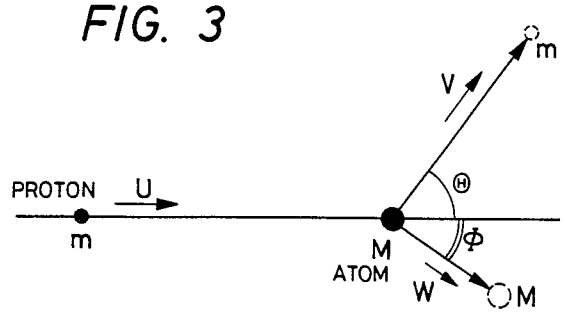
FIG. 3 is a velocity diagram both before and after a collosion between an atom with mass M and a proton with mass m.
Figure 4:
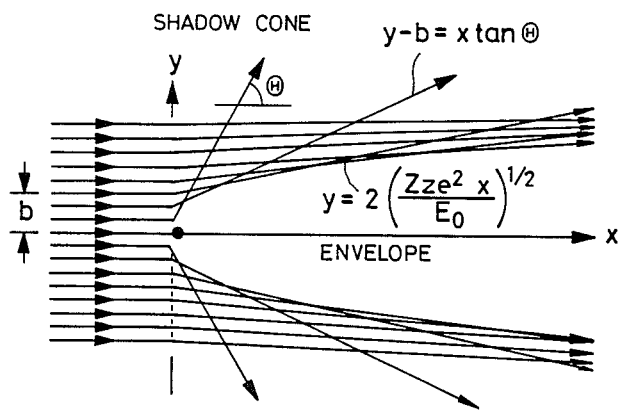
FIG. 4 shows a shadow cone created in the forward direction when protons are scattered by an atom.
Figure 5:
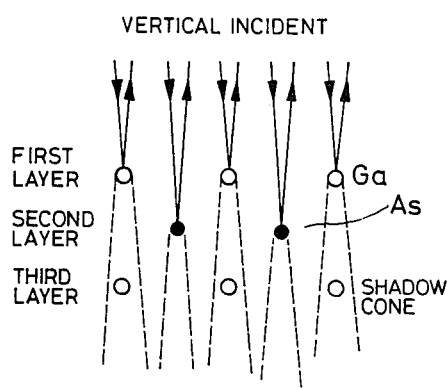
FIG. 5 is a sketch of the top few layers of GaAs crystal showing how proton beams that are incident and scattered perpendicularly to the crystal surface in PELS.
Figure 6:
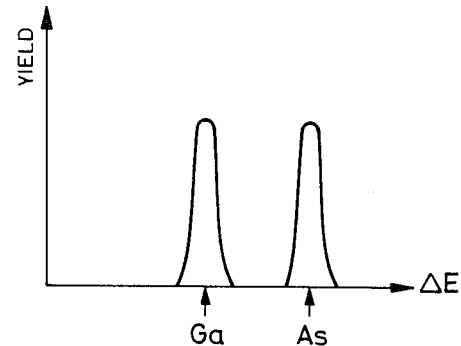
FIG. 6 is a diagram of proton energy loss that occurs in PELS when proton beams are incident in the direction indicated in FIG. 5.
Figure 14:
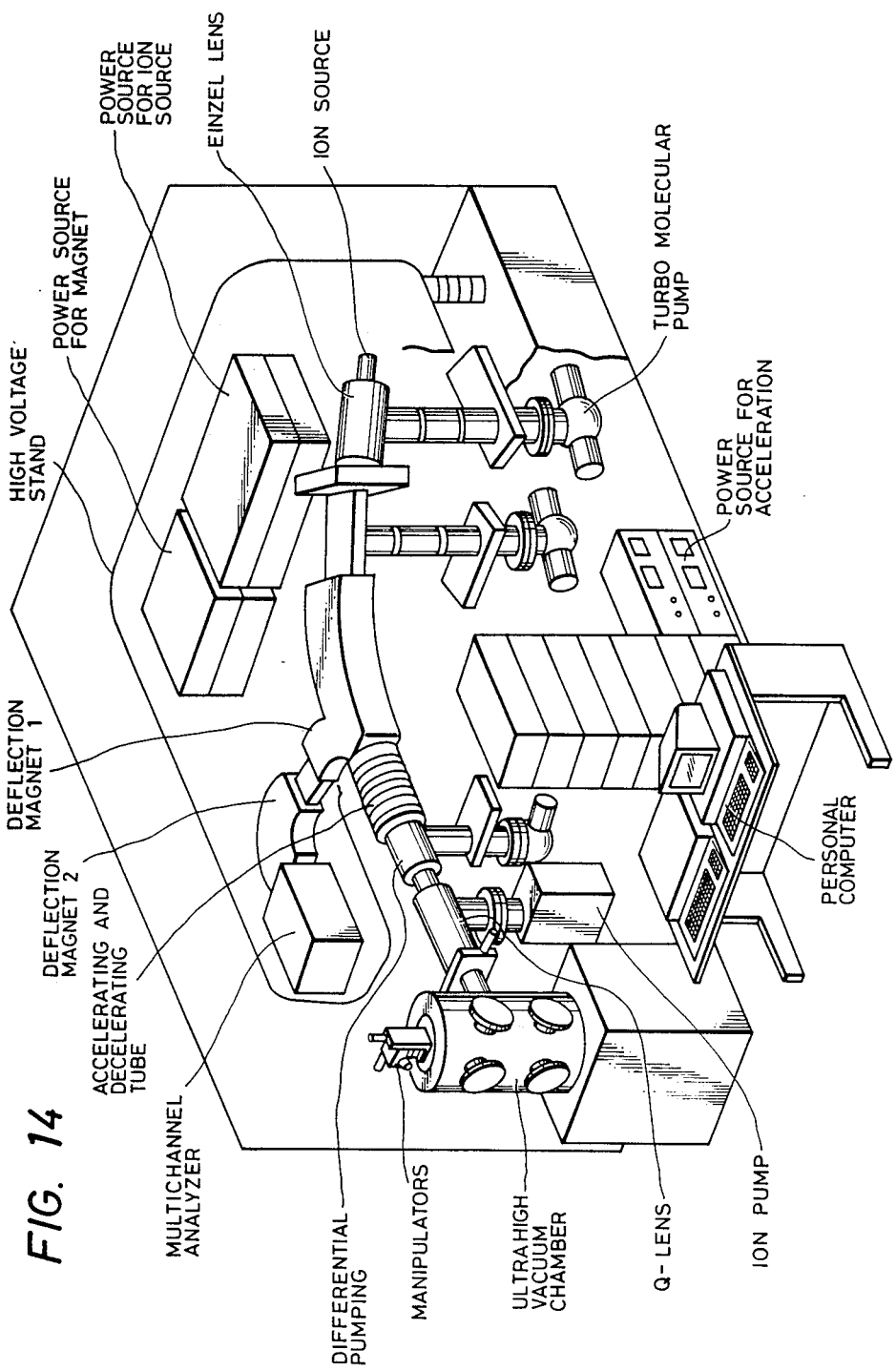
FIG. 14 is a perspective view showing the general layout of a practical version of PELS equipment.

The results of the above determination are shown in FIG. 2. If Vex is high, a broad range of mass numbers ($\Gamma = 11-209$) can be covered. If qVex=34.2 keV, the present invention is effective for almost all elements. However, the resolution of atoms with large mass numbers is low if Vex is high. This is because atoms with large mass numbers, even if protons are scattered, cause only a very small amount of energy loss $\Delta E$ and hence produce only a small difference in position X.

Atoms with larger mass numbers can be detected if Vex is reduced. However, Ro includes Vex, so a change in Vex will result in a corresponding change in Ro and Eq. (36) is not established. In this case, the magnetic field B is appropriately adjusted to render Ro constant.

It is desired to selectively detect atoms even if they have mass numbers (M/m) close to each other. The smallest difference, $\Delta\Gamma$, in mass number that allows for separation of two atoms is called the mass resolution, which is usually expressed by $\Gamma/\Delta\Gamma$, or multiplied by m into M/$\Delta$M. This expression means that a particular atom with mass M can be detected separately from an atom with mass (M+$\Delta$M).

Figure 17:
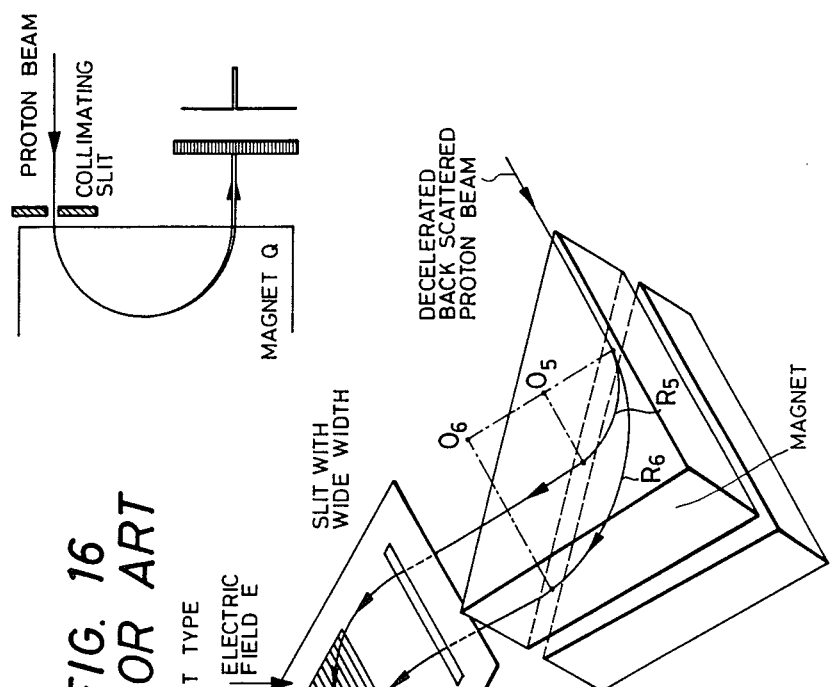
FIG. 17 is a plan view showing how scattered proton beams are collimated with a slit.

To achieve this separation, a collimating slit having a width of x is positioned in the path of a proton beam as shown in FIG. 17. If x is small, high mass resolution is attained. The resolution attained can be defined as follows:

$$\frac{M}{\Delta M} = \frac{2(R_2 - R_1)}{X} \cdot \frac{M_2}{M_2 - M_1} \quad (37)$$

where $R_1$ and $R_2$ are the radii of curvature of the circular paths traveled by protons in magnet Q after they were scattered ($\theta = 180°$) by atoms with mass of $M_1$ and $M_2$.

Figure 18:
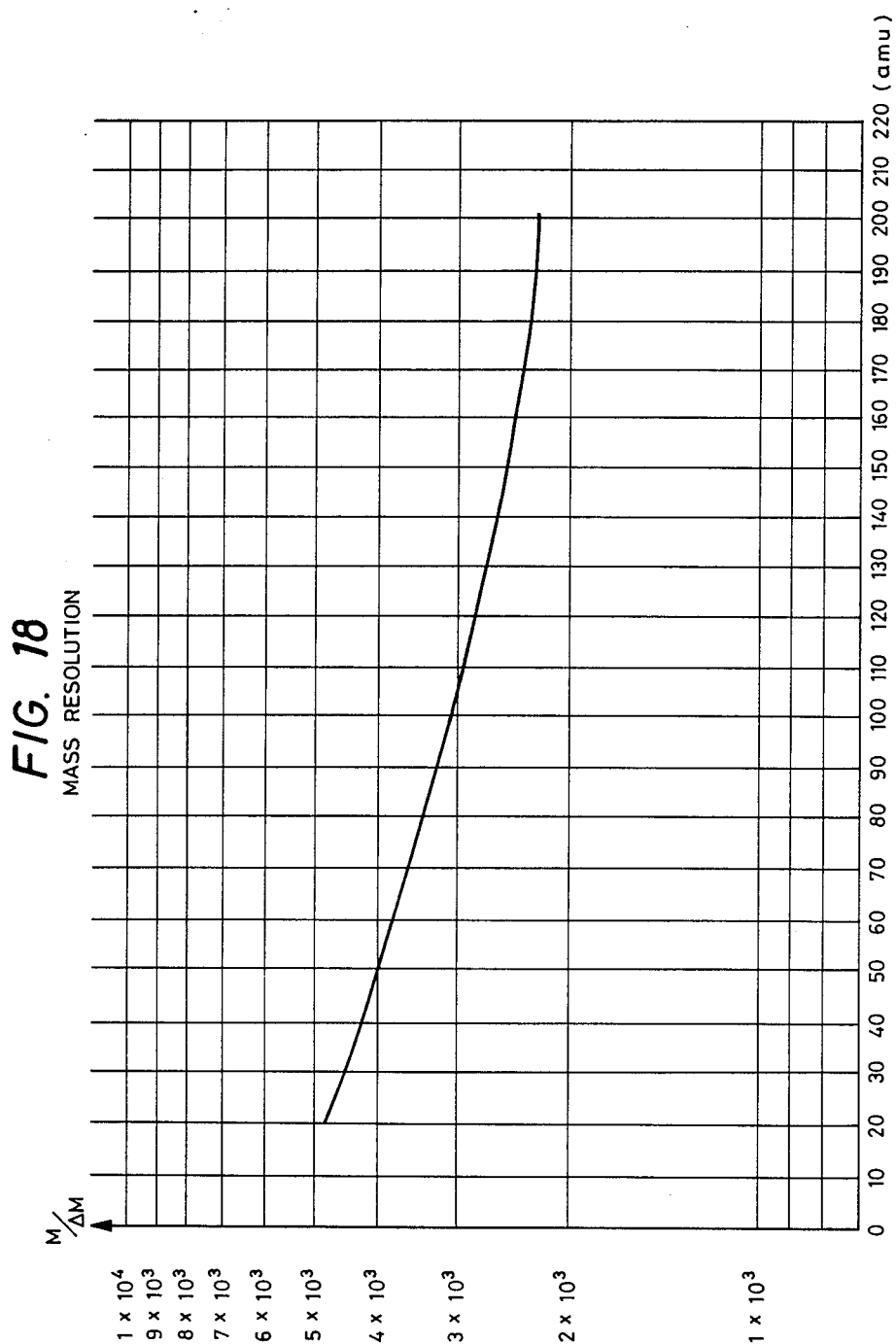
FIG. 18 is a graph showing the mass resolution vs. mass number for various atoms analyzed with the apparatus of the present invention.

The value of x is determined by the width of the slit shown in FIG. 17 or the cell width of an individual microchannel in the microchannel plate. The slit width is a predominant factor since the cell width is extremely small (less than 100 microns). Calculations of M/$\Delta$M from Eq. (37) were conducted using a slit width of 0.5 mm (500 microns) and assuming $M_2 - M_1 = 1$. Substantially the same results are attained even if the value of $M_2 = M_1$ is 2 or 3, but for the sake of simplicity, the value 1 was selected. The results are shown in FIG. 18, from which it can be seen that a higher mass resolution can be attained for atoms with smaller mass M (i.e., small ΔE). This is because the square root of energy Ea is proportional to R in a magnetic field.

This can be explained mathematically as follows.

Looking at Eqs. (31), (32), (34) and (35), the following substitution may be used:

$$\zeta = \frac{4E_o}{q V_{ex}} \quad (38)$$

$$\text{Then, } R = R_o \left(1 - \frac{\zeta \Gamma}{(1 + \Gamma)^2}\right)^{\frac{1}{2}} \quad (39)$$

Differentiating Eq. (39) with respect to $$\frac{dR}{d\Gamma} = \frac{\zeta R_o}{2} \frac{(\Gamma - 1)}{(\Gamma + 1)^3} \left(1 - \frac{\zeta \Gamma}{(1 + \Gamma)^2}\right)^{-\frac{1}{2}} \quad (40)$$

When substitutions $\Gamma/\Delta\Gamma = M/\Delta M$ and $dR = x$ are used, $$\frac{M}{\Delta M} = \frac{\zeta R_o}{2x} \frac{\Gamma(\Gamma - 1)}{(\Gamma + 1)^3} \left(1 - \frac{\zeta \Gamma}{(1 + \Gamma)^2}\right)^{-\frac{1}{2}} \quad (41)$$

Eq. (41) clearly shows that M/ΔM decreases with increase in Γ.

The case where a scattered proton beam is launched into the magnet at 90° has been described with reference to FIG. 1. It should be noted, however, that the present invention also works effectively even if α is not 90°. the radius R does not include α. Since side NJ forms angle α with respect to beam line WΣ, the central angle of an arc described by the scattered beam before it leaves the magnet is 2α. The beam emerges from the magnet at the same angle of α with respect to side NJ. Therefore, the microchannel plate is tilted by (90°−2α) with respect to side NJ. In this case, the position X to be detected is expressed not by Eq. (28) but by:

$$X = 2R_o \left(1 - \frac{\Delta E}{qV_{ex}}\right)^{\frac{1}{2}} \sin^2 \alpha + (\text{const}) \quad (42)$$

Figure 19:
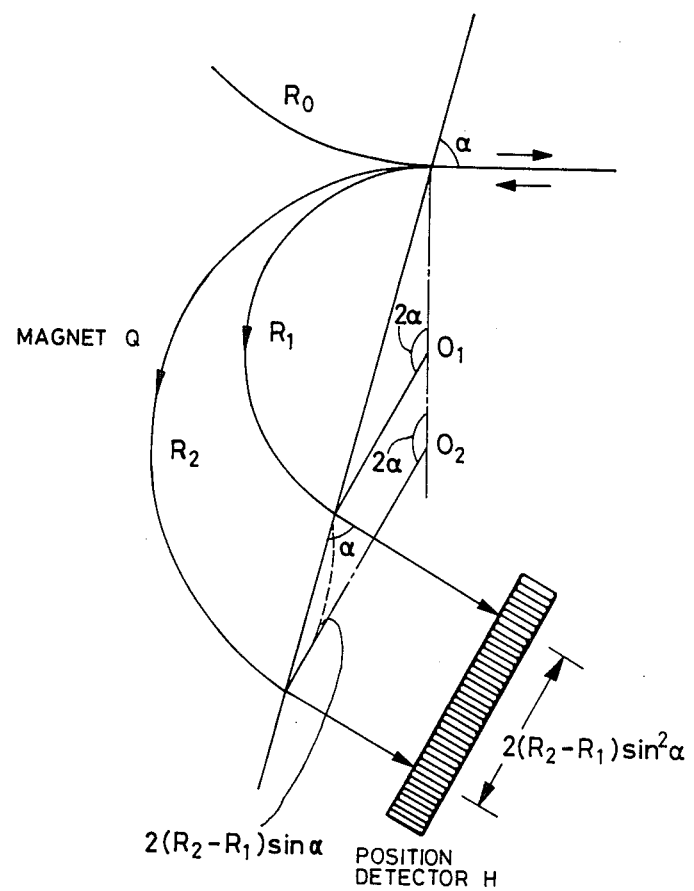
FIG. 19 is a sketch showing a layout of a magnetic position detector for the case where $\alpha \neq 90°$.

FIG. 19 illustrates a layout of a magnetic position detector for the general case where α≠90°.

Figure 16:
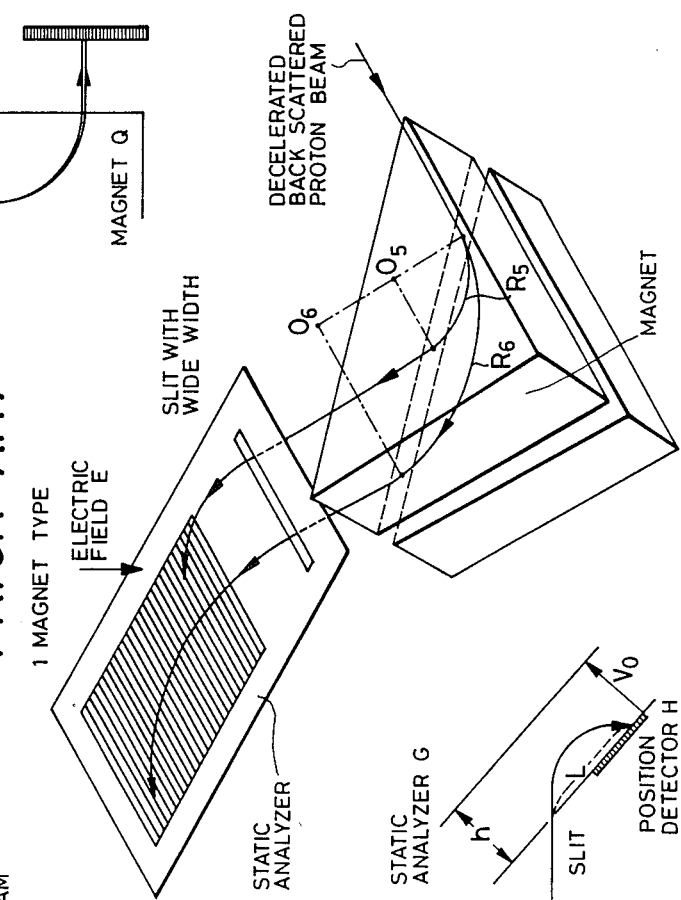
FIG. 16 is a plan view showing schematically a prior art electrostatic analyzer system using a single magnet.
Figure 15:
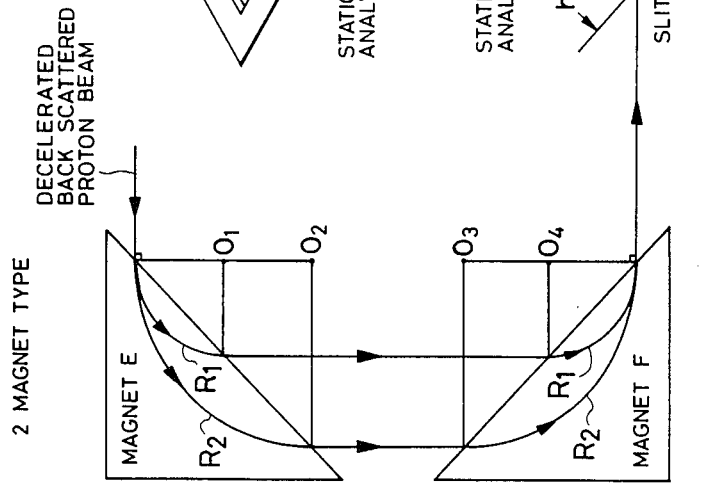
FIG. 15 is a plan view showing schematically a prior art electrostatic analyzer system using two magnets.

As evident from the foregoing the present invention has several advantages. In an electrostatic analyzer, a proton beam is launched at an angle between two parallel electrodes. In order to enable energy measurements even for rapidly moving protons, the distance between electrodes must be increased. This makes the electrostatic analyzer an unduly bulky apparatus. By eliminating the use of an electrostatic analyzer in the manner of the present invention, the size of the PELS appartus is reduced. As an attendant advantage, the load on the evacuation unit can also be reduced. Moreover, in the present invention, a single magnet suffices for energy measurements. Since the magnetic gap may be very narrow, only a small space is required for magnet installation. Furthermore, by decreasing the ion extracting voltage Vex, the spectrum for detecting of heavy elements (large M and small ΔE) can be expanded. Moreover, if a collimator is inserted as shown in FIG. 17, fine spectra (i.e., high resolution) can be attained although low yield results. Compared with the one-magnet system shown in FIG. 16, the width of a microchannel plate is small enough to offer an economical apparatus. Also, the number of operating parameters that need adjustment is reduced. The voltage, V₀, of an electrostatic analyzer is not a design parameter. The combination of ion extracting voltage Vex with magnetic field B leads to simplified manipulation of the apparatus.

What is claimed is:

1. A surface analyzer for analyzing the atomic composition of the surface of a sample comprising:
   an ion source for generating protons;
   accelerating/decelerating means for accelerating protons moving therethrough in a first direction toward the sample and decelerating protons moving therethrough in a second direction opposite to the first direction and away from the sample after collision with the sample;
   a microchannel plate for multiplying secondary electrons generated by protons incident thereon;
   a position detector for receiving said multiplied electrons and for indicating the position of said received multiplied electrons; and
   a magnet interposed between said ion source and said accelerating/decelerating means and between said accelerating/decelerating means and said microchannel plate, said magnet for directing protons from said ion source to said accelerating/decelerating means for acceleration thereby prior to collision with the sample, and for directing protons decelerated by said acceleration/deceleration means after collision with the sample to a position on said microchannel plate at a low energy level such that the kinetic energy and energy loss of the protons following collision with the sample are indicated by the position of the emission of said multiplied protons from said microchannel plate as detected by said position detector.

2. A surface analyzer according to claim 1, wherein said protons directed to said microchannel plate have an energy of approximately 0.5 KeV or less.

3. A surface analyzer for analyzing the atomic composition of the surface of a sample comprising:
   an ion source for generating protons;
   accelerating/decelerating means for accelerating protons moving therethrough in a first direction toward the sample and decelerating protons moving therethrough in a second direction opposite to the first direction and away from the sample after collision with the sample and scattering at an angle of 180° with respect to the sample;
   a magnet for directing protons from said ion source to said accelerating/decelerating means for acceleration toward the sample and for forming low energy parallel beams of the protons passing through the accelerating/decelerating means following scattering at an angle of 180° after collision with the sample; and
   position detecting means for receiving said parallel proton beams and for indicating the position at which said parallel proton beams are received such that the kinetic energy and energy loss of protons that collide with the sample and are scattered at an angle of 180° may be determined.

4. A surface analyzer according to claim 3, wherein said magnet has a magnetic field of variable strength and an invariable radius of curvature of incident proton beams.

5. A surface analyzer according to claim 4, wherein said position detecting means includes a microchannel plate.

6. A surface analyzer according to claim 3, wherein said parallel beams of protons formed by said magnet have an energy level of approximately 0.5 KeV or less.

* * * * *